United States Patent
Koizumi et al.

(10) Patent No.: US 7,375,455 B2
(45) Date of Patent: May 20, 2008

(54) ULTRASONIC MOTOR DRIVING DEVICE AND ULTRASONIC DIAGNOSIS APPARATUS

(75) Inventors: Jun Koizumi, Yokohama (JP); Kazuyoshi Irioka, Sagamihara (JP); Masao Onozuka, Kawasaki (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 163 days.

(21) Appl. No.: 10/566,981

(22) PCT Filed: Aug. 6, 2004

(86) PCT No.: PCT/JP2004/011639

§ 371 (c)(1),
(2), (4) Date: Feb. 2, 2006

(87) PCT Pub. No.: WO2005/015728

PCT Pub. Date: Feb. 17, 2005

(65) Prior Publication Data

US 2006/0250046 A1 Nov. 9, 2006

(30) Foreign Application Priority Data

Aug. 8, 2003 (JP) ............................ 2003-290801

(51) Int. Cl.
*H01L 41/09* (2006.01)
*H02N 2/14* (2006.01)
(52) U.S. Cl. ........................ 310/316.02; 310/316.01; 310/334
(58) Field of Classification Search ............ 310/316.02, 310/322, 334, 335, 316.01, 317
See application file for complete search history.

(56) References Cited

U.S. PATENT DOCUMENTS

| | | | |
|---|---|---|---|
| 5,487,386 A | 1/1996 | Wakabayashi et al. | |
| 5,631,517 A | 5/1997 | Kato et al. | |
| 6,213,948 B1 * | 4/2001 | Barthe et al. | 600/445 |
| 6,384,511 B1 | 5/2002 | Sakai | |
| 6,441,534 B2 * | 8/2002 | Iino et al. | 310/316.01 |

FOREIGN PATENT DOCUMENTS

| | | |
|---|---|---|
| JP | 02261077 | 10/1990 |
| JP | 05328761 | 12/1993 |
| JP | 07322658 | 12/1995 |

OTHER PUBLICATIONS

PCT International Search Report dated Nov. 22, 2004.

* cited by examiner

*Primary Examiner*—Darren Schuberg
*Assistant Examiner*—Derek J Rosenau
(74) *Attorney, Agent, or Firm*—Dickinson Wright, PLLC

(57) ABSTRACT

An ultrasonic motor drive device capable of prolong the service life of an ultrasonic motor by preventing the motor from being unstably operated when the motor is driven at a lower speed of at least two speeds. When the ultrasonic motor (3) is driven at a rather low speed in normal driving, the motor can be prevented from being unstably operated by its driving at a rather low speed by driving the motor at a rather high speed for each specified interval. Thus, the service life of the ultrasonic motor can be increased.

4 Claims, 7 Drawing Sheets

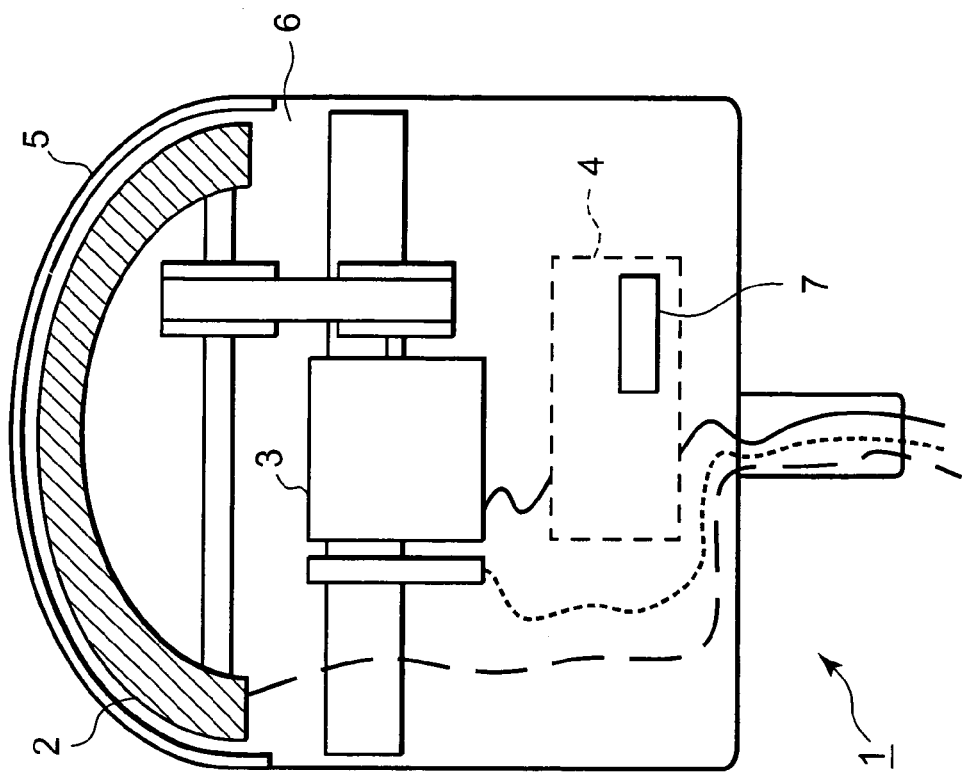
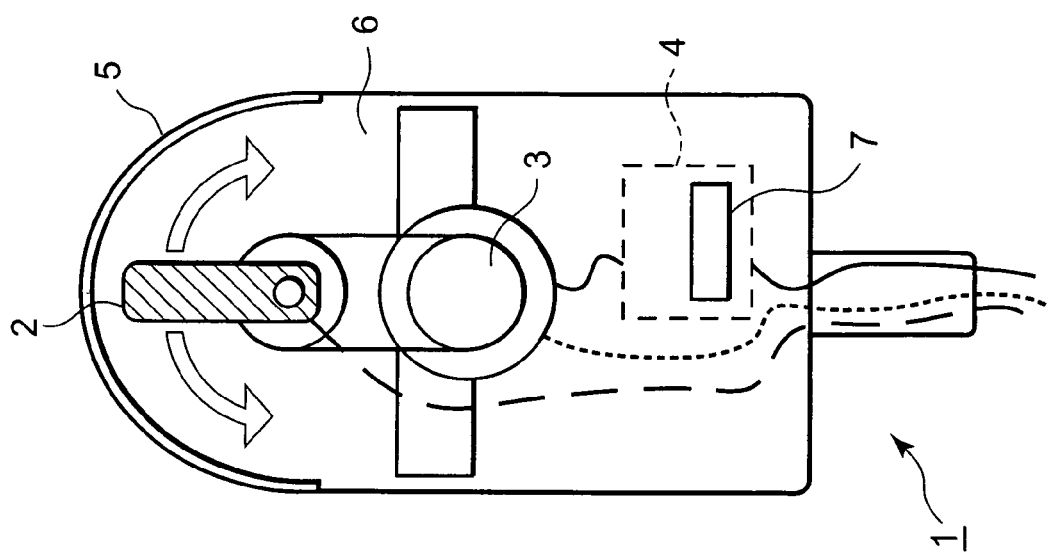

ULTRASONIC MOTOR DRIVING DEVICE AND ULTRASONIC DIAGNOSIS APPARATUS

TECHNICAL FIELD

The present invention relates to an ultrasonic motor driving device for driving an ultrasonic motor.

The present invention also relates to an ultrasonic diagnostic device for obtaining three-dimensional images by scanning sonic elements by driving an ultrasonic motor.

BACKGROUND ART

An ultrasonic motor generally has a construction such as that described in Patent Reference 1, below. Hereafter, this construction is explained, with reference to the rough cross-sectional diagram shown in FIG. 7. In this example, stator 52 and rotor 53 are constructed such as to be pressurized by spring 54 and appressed. The surface of stator 52 which is in contact with rotor 53 is formed as a pectinate, and piezoelectric ceramic 51 is provided on the surface on the opposite side thereof. In a construction as such, a traveling wave is generated in piezoelectric ceramic 51 when an ultrasonic wave is impressed thereto, and this traveling wave is transmitted to rotor 53 via the pectinate surface and the rotor 53 rotates in the direction of the traveling wave (straight forward movement in the case of a linear motor). Although, the zoom lens of a camera is common as a use of the ultrasonic motor, the rotor 53 is rotationally-driven at a comparatively high speed (for example, 40 rpm) when utilized for such uses.

Patent Reference 1: Japanese Patent Application Publication H2-261077

In conventional three-dimensional ultrasonic diagnostic devices, generally, a three-dimensional image with three directions of the arc direction of a sonic element, the rotational scanning direction and the depth direction are obtained by performing scanning with the arc shaped sonic element rotated in a direction perpendicular to the arc direction. In addition, although, in recent years, the ultrasonic motor has been utilized as a driving means for rotating sonic elements, the rotor 53 is rotationally-driven at a comparatively low speed (for example, 10 rpm or less) when utilized for such uses.

However, when such a conventional ultrasonic motor is driven for a long period of time at a relatively low speed, there occur problems such that roughness occurs on the surface of the pectinate stator 52 at the side which is in contact with the rotor 53, and also, fine particles of the stator 52 are transferred to the contact surface of the rotor 53 so that stable operation will not be obtained, resulting in a short life. Furthermore, in an ultrasonic diagnostic device utilizing this ultrasonic motor, a three-dimensional image cannot be obtained because stable operation can no longer be attained.

DISCLOSURE OF THE INVENTION

In light of the foregoing issues, an object of the present invention is to provide an ultrasonic motor driving device which prevents unstable operation when the ultrasonic motor is driven at a low speed, out of at least two types of speeds, and aims to extend life.

The object of the present invention is to also provide an ultrasonic diagnostic device which prevents unstable operation of the ultrasonic motor without affecting diagnostic operation by the user and aims to extend life.

In order to achieve the foregoing objects, the present invention, in an ultrasonic motor driving device for driving an ultrasonic motor, has a speed control means for driving the ultrasonic motor at at least two types of speeds and has a construction characterized by driving at a low speed, the slower out of the two types of speeds, during normal drive.

Through the forgoing construction, unstable operation can be prevented when the ultrasonic motor is driven at the lower speed out of at least two types of speeds and life extension can be attempted.

In addition, in order to achieve the foregoing objects, the present invention, in an ultrasonic diagnostic device for obtaining three-dimensional images by scanning sonic elements by driving an ultrasonic motor, has a construction, wherein whether or not the ultrasonic motor was driven for a predetermined period of time, at the lower speed out of at least two types of speeds, when the power switch of the ultrasonic diagnostic device has been turned OFF, is determined, and if it was driven, the ultrasonic motor is driven at the higher speed out of at least two types of speeds, for an arbitrarily set period of time.

Through the foregoing construction, unstable operation of the ultrasonic motor can be prevented without affecting the diagnostic operations by the user and life extension can be attempted.

In addition, in order to achieve the foregoing objects, the present invention, in an ultrasonic diagnostic device for obtaining three-dimensional images by scanning sonic elements by driving an ultrasonic motor, has a construction, has a construction, wherein whether or not the ultrasonic motor was driven for a predetermined period of time, at the lower speed out of at least two types of speeds, when the screensaver of the monitor which shows the three-dimensional image has been turned ON, is determined, and if it was driven, the ultrasonic motor is driven at the higher speed out of at least two types of speeds.

Through the foregoing construction, unstable operation of the ultrasonic motor can be prevented without affecting the diagnostic operations by the user and life extension can be attempted.

In addition, in order to achieve the foregoing objects, the present invention, in an ultrasonic diagnostic device for obtaining three-dimensional images by scanning sonic elements by driving an ultrasonic motor, has a construction, has a construction, wherein whether or not the ultrasonic motor was driven for a predetermined period of time, at the lower speed out of at least two types of speeds, is determined when the power switch is turned ON for the first time within one day, and if it was driven, the ultrasonic motor is driven at the higher speed out of at least two types of speeds.

Through the foregoing construction, unstable operation of the ultrasonic motor can be prevented without affecting the diagnostic operations by the user and life extension can be attempted.

In addition, in order to achieve the foregoing objects, the present invention, in an ultrasonic diagnostic device for obtaining three-dimensional images by scanning sonic elements by driving an ultrasonic motor, has a construction, has a construction, wherein the user is asked whether or not the driving function in the lower speed out of at least two types of speeds should be turned on, by driving the ultrasonic motor at the higher speed out of at least two types of speeds, when the ultrasonic motor is driven for a predetermined period of time at the lower speed out of at least two types of speeds, and if the user selects this function, a means for turning on this function is provided.

Through the foregoing construction, unstable operation of the ultrasonic motor can be prevented without affecting the diagnostic operations by the user and life extension can be attempted.

According to the present invention, unstable operation of the ultrasonic motor can be prevented when the ultrasonic motor is driven at the lower speed out of at least two types of speeds and life extension can be attempted.

In addition, according to other embodiments of the present invention, unstable operation of the ultrasonic motor can be prevented without affecting the diagnostic operations by the user and life extension can be attempted.

BRIEF DESCRIPTION OF THE DRAWINGS

FIG. 1A is an internal configuration diagram of an ultrasonic probe according to the present invention, viewed from the side;

FIG. 1B is a an internal configuration diagram of the ultrasonic probe according to the present invention when viewed from the front;

BEST MODE FOR CARRYING OUT THE INVENTION

Descriptions are hereinafter given of the embodiments of the present invention, with reference to the drawings.

Figure 2:
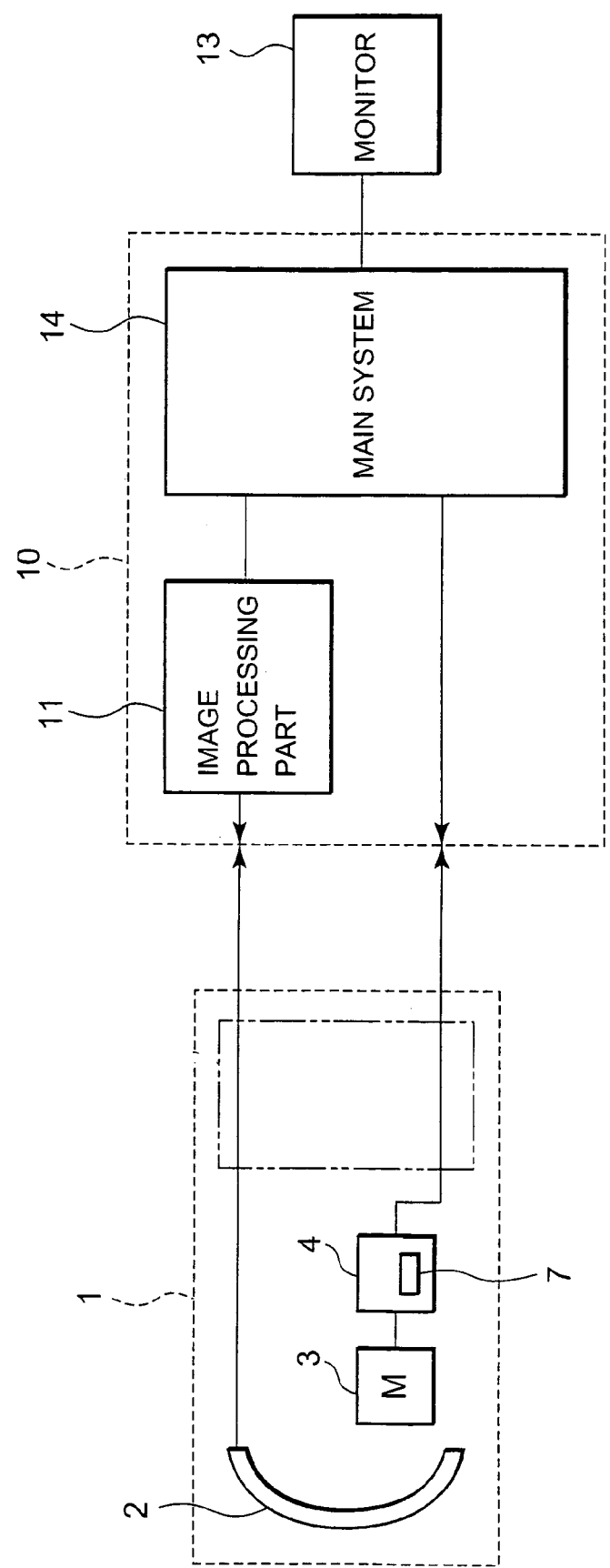
FIG. 2 is a block diagram showing an ultrasonic diagnosis device according to the present invention.

FIG. 1A shows the internal configuration of an ultrasonic probe 1 according to the present invention when viewed from the side, and FIG. 1B shows the internal configuration of the ultrasonic probe 1 when viewed from the front. In FIG. 1A and FIG. 1B, the ultrasonic probe 1 is connected to an ultrasonic diagnostic device main unit 10, shown in FIG. 2, via cable, such as to enable connection and detachment. In the inner part which is separated from the outer part by window 5 at the tip of the ultrasonic probe 1, an arc-shaped sonic element 2 is supported by an ultrasonic motor (M) 3, such as to enable back and forth rotation within coupling fluid 6 in the direction perpendicular to the arc direction. Ultrasonic motor 3 is driven by providing driving electrical power from the ultrasonic diagnostic device main unit 10, shown in FIG. 2, via an ultrasonic motor driving device 4 which contain a speed control means 7. Then, as shown in FIG. 2, the output of sonic element 2 is transmitted to the ultrasonic diagnostic device main unit 10, processed by an image processing part 11 into a three-dimensional image in the arc direction, scanning direction and depth direction of the sonic element 2, and this three-dimensional image is shown on monitor 13.

Figure 7:
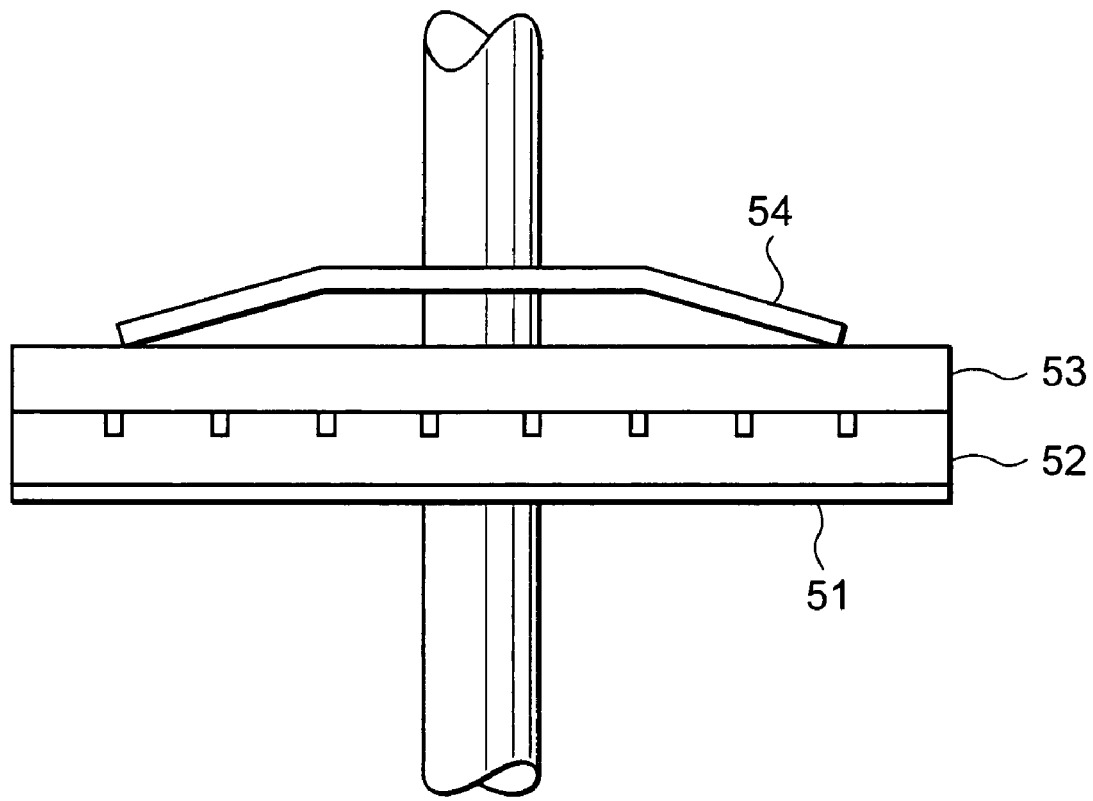
FIG. 7 is an explanatory diagram showing a rotation-type as an example of the operational principles of an ultrasonic motor.

Here, when an ultrasonic motor, such as that shown in FIG. 7, is driven at a comparatively low speed (for example, 10 rpm or less), problems occur in that, roughness occurs on the pectinate surface of stator 52, on the side in contact with rotor 53, and in addition, a stable operation can no longer be attained because the fine particles of this stator 52 are transferred to the contact surface of the rotor 53, and life is shortened. The reason for this is thought to be because the surface of the stator 52 on the side in contact with rotor 53 is formed as a pectinate and stator 52 and rotor 53 are appressed, in order to transmit the traveling wave generated in stator 52 to rotor 53.

Incidentally, it has been found that, if an ultrasonic motor which cannot be stably operated is rotated at a comparatively high speed (for example, 40 rpm), the roughness of the pectinate surface of stator 52 and the contact surface of rotor 53 can be improved, such as to return to the original state, and rotation becomes normal. The reason for this is thought to be because an abrasive effect on the foregoing contact surface occurs due to high-speed rotation, reducing the roughness, and additionally, fine particles are released into the grooves between the teeth of the comb. Thus, the present invention has a speed control means 7 for driving the ultrasonic motor by switching between at least two types of speeds, and when operating the ultrasonic motor, if a comparatively low-speed normal operation is performed for a predetermined period of time, a comparatively high-speed operation (hereinafter, treatment) is performed. Although speed control means 7 is provided within the ultrasonic probe 1 in FIG. 1A and FIG. 1B, it can also be provided within ultrasonic diagnostic device main unit 10.

First Embodiment

Figure 3:
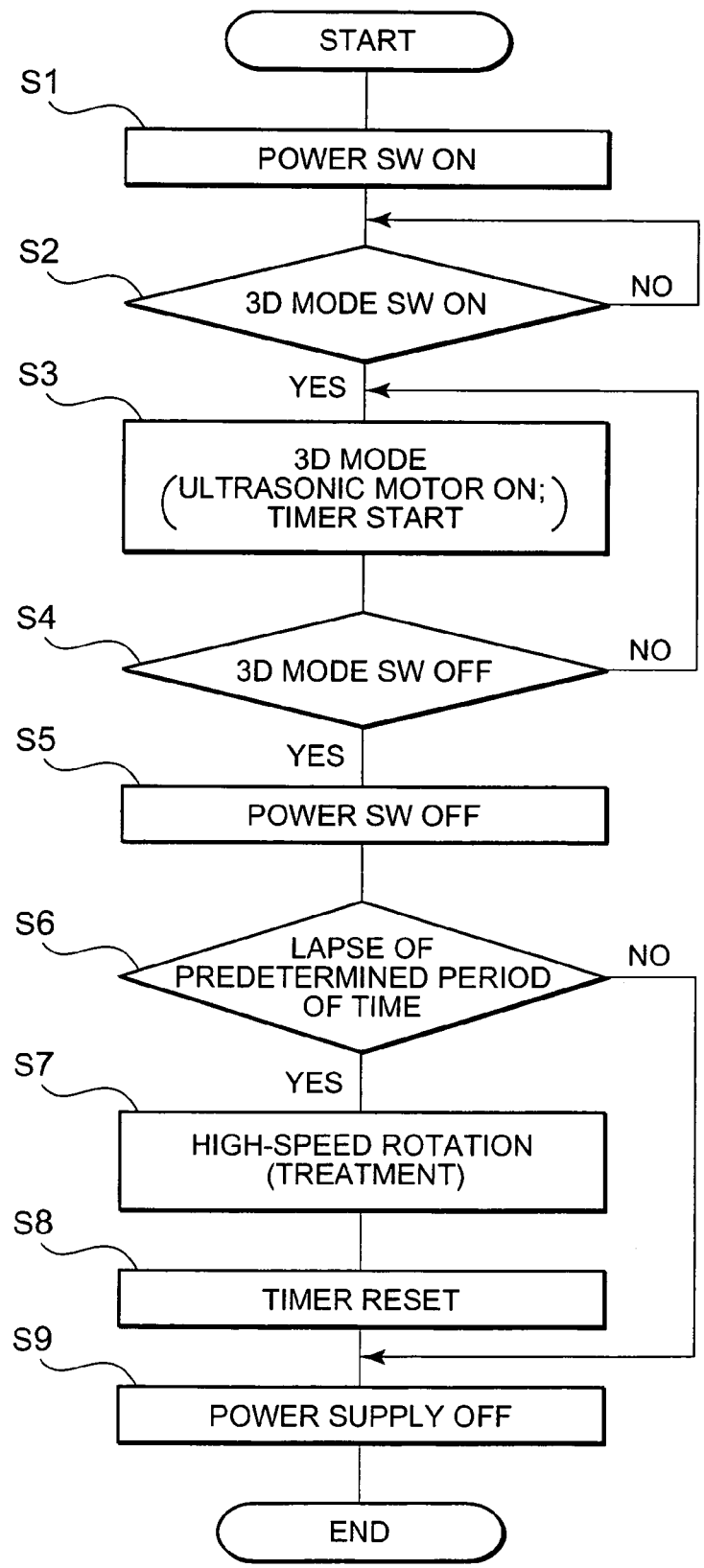
FIG. 3 is a flowchart explaining the processing of the ultrasonic diagnosis device according to a first embodiment of the present invention.

FIG. 3 is a flowchart showing an embodiment applied to the ultrasonic diagnostic device shown in FIG. 1A, FIG. 1B, and FIG. 2, as one example, and the operation of a main system 14 of the ultrasonic diagnostic device main unit 10. Incidentally, if the device-side performs a treatment on its own while the user is performing an ultrasonic diagnosis, this interferes with the diagnosis. Therefore, in a first embodiment, under the premise that the user is not performing a diagnosis, the speed control means 7 switches and controls the speed from low-speed to high-speed when the user has turned the power SW off, and the treatment is performed.

In FIG. 3, first, the power SW (unillustrated) of the ultrasonic diagnostic device main unit 10 is turned ON (step S1), a state enabling ultrasonic diagnosis is entered; furthermore, when 3D mode SW (unillustrated) is turned ON (Y in step S2), ultrasonic diagnosis in 3D mode begins, ultrasonic motor 3 is ON, and the timer starts (step S3). Next, whether or not the 3D mode SW has been turned OFF is determined (step S4), and if it is not OFF, ultrasonic diagnosis in 3D mode is continued (step S4→S3); on the other hand, if 3D mode SW is turned OFF (step S4→S5), the timer is turned OFF, and the amount of time the ultrasonic diagnosis was performed is recorded. This timer records the cumulative time ultrasonic diagnosis was performed. If ultrasonic diagnosis in 3D mode completed and the power SW of the ultrasonic diagnostic device is subsequently turned OFF (step S5), treatment is performed (step S6 S7), the timer is reset (step S8), and power supply to the ultrasonic diagnostic device is turned OFF (step S9), only when the cumulative time recorded by the timer exceeds a predetermined period of time (for example 90 minutes). If the cumulative time recorded by the timer does not exceed a predetermined period of time (step S6→S9), power supply to the ultrasonic diagnostic device is turned OFF (step S9) without performing treatment.

Through the foregoing construction, unstable operation of the ultrasonic motor can be prevented without affecting the diagnostic operations by the user and life extension can be attempted.

Second Embodiment

Figure 4:
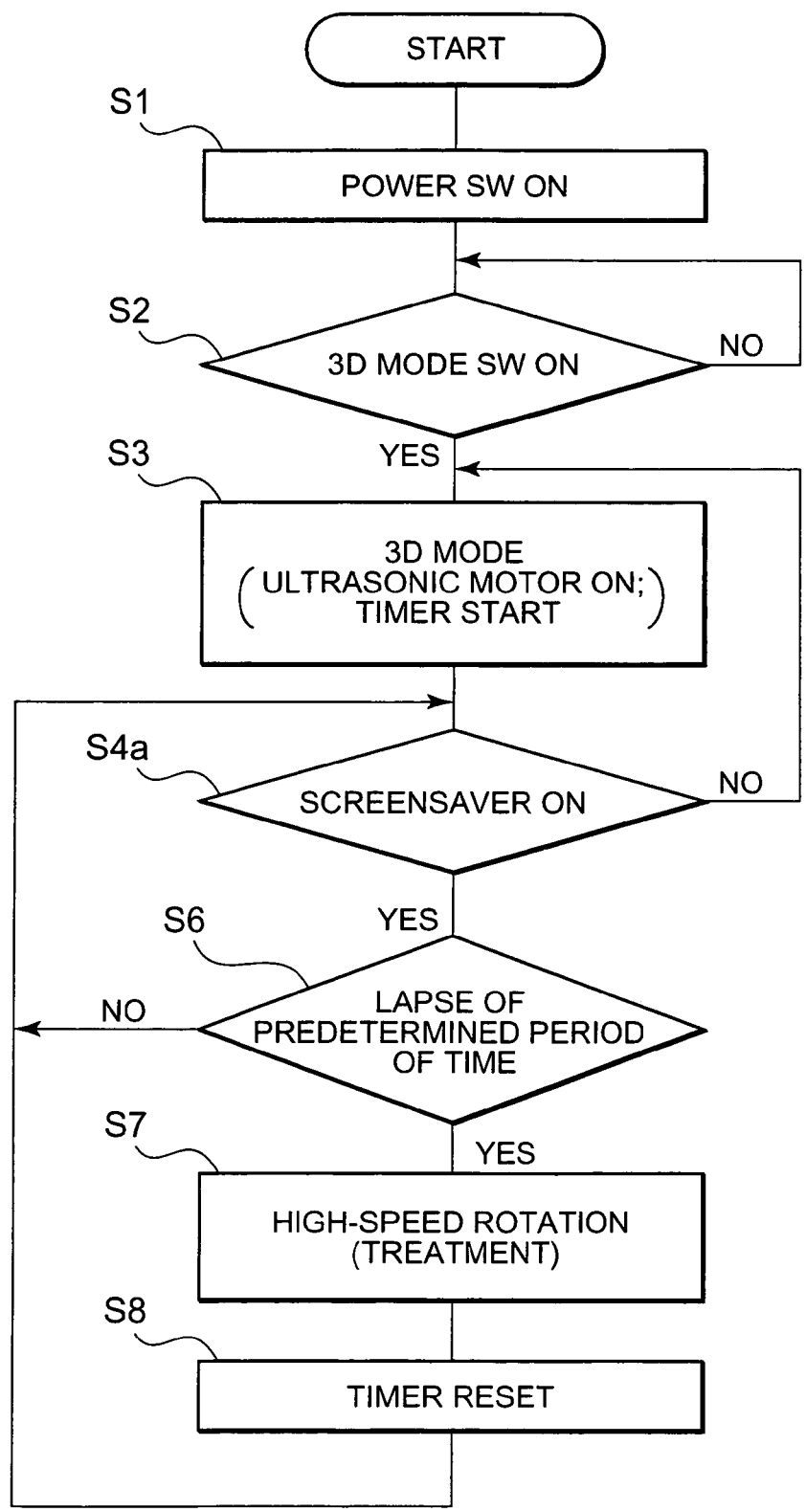
FIG. 4 is a flowchart explaining the processing of the ultrasonic diagnosis device according to a second embodiment of the present invention.

Next, a second embodiment is described with reference to FIG. 4. In the second embodiment, under the premise that the user is not performing a diagnosis, treatment is performed when the screensaver function of monitor 13 is in operation. In FIG. 4, first, the power SW (unillustrated) of the ultrasonic diagnostic device main unit 10 is turned ON (step S1); furthermore, when 3D mode SW (unillustrated) is turned ON (Y in step S2), ultrasonic diagnosis in 3D mode begins, ultrasonic motor 3 is ON, and the timer starts (step S3). Next, whether or not the screensaver has been turned ON is determined (step S4a), and if it is not ON, ultrasonic diagnosis in 3D mode is continued (step S4a→S3); on the other hand, if the screensaver is turned ON, it is determined whether or not the predetermined period of time elapsed on the timer (step S4a→S6). Then, if the predetermined period of time has elapsed, treatment is performed (step S7), the timer is reset (step S8), and subsequently, the processing returns to step S4a. This predetermined period of time can be determined based on experiments or can be set arbitrarily by the user, within a range which does not affect the diagnostic operation, by providing a setting input means.

Through the foregoing construction, unstable operation of the ultrasonic motor can be prevented without affecting the diagnostic operations by the user, even if it is in the middle of a day, and life extension can be attempted. The time remaining until the completion of a treatment or a warning display can be shown by numbers or an indicator. If the screensaver is terminated, the treatment can be forcibly terminated, or the user can be urged to wait by displaying the time until treatment completion.

Third Embodiment

Figure 5:
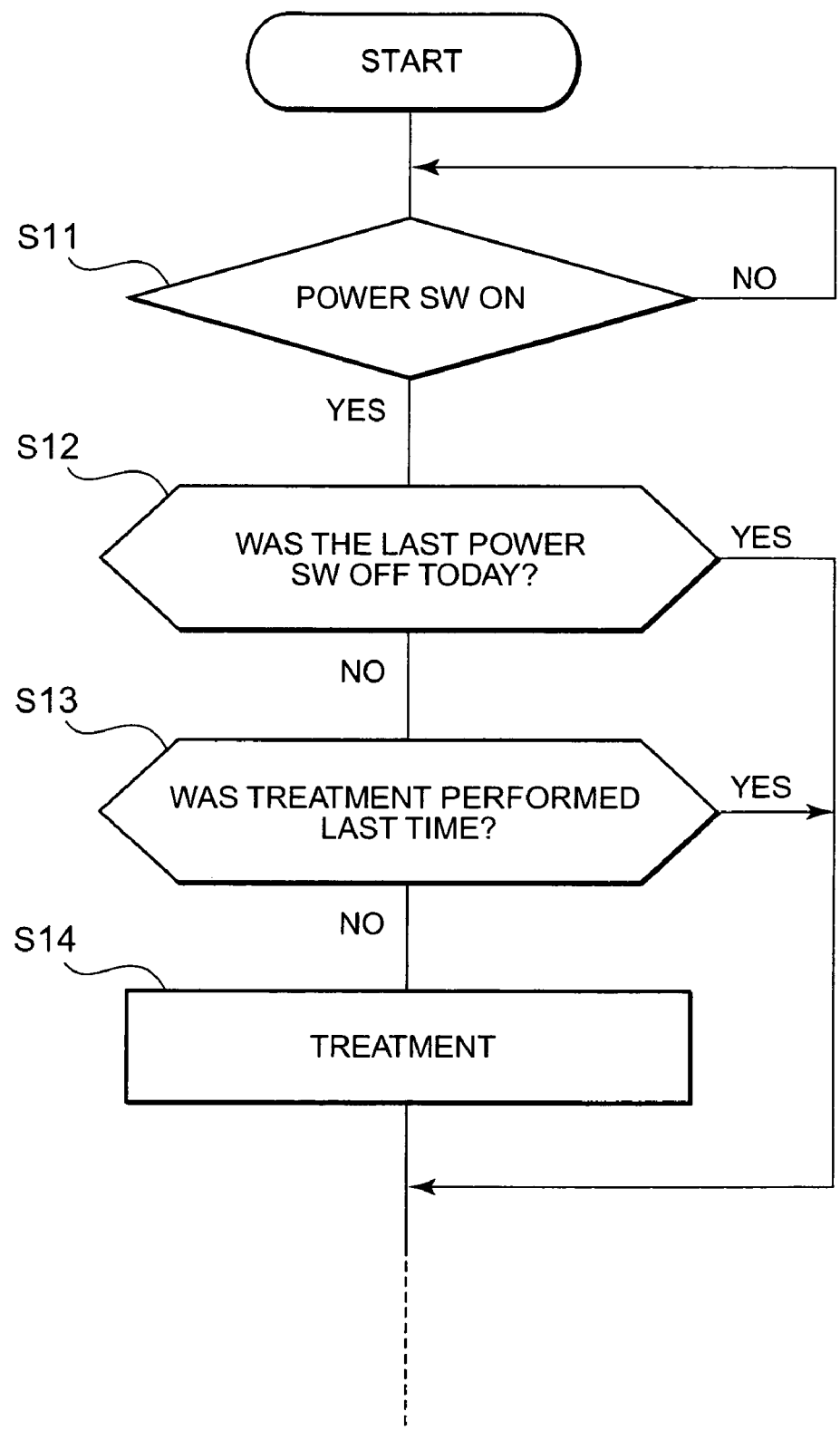
FIG. 5 is a flowchart explaining the processing of the ultrasonic diagnosis device according to a third embodiment of the present invention.

Next, a third embodiment is described with reference to FIG. 5. In the third embodiment, treatment is performed immediately after the user has turned the power SW ON for the first time within one day. In FIG. 5, first, when the power SW (unillustrated) of the ultrasonic diagnostic device main unit 10 is turned ON (Y in step S11), it is determined whether or not the previous power SW OFF was today, or in other words, whether or not it was yesterday or before (step S12). Then, if the previous power SW OFF was yesterday or before, it is determined whether or not treatment was previously performed (step S12→S13), and if it was not performed, treatment is performed (step S13→S14). The determination step of step S13 can be omitted, and treatment can be performed unconditionally when the user has turned the power SW ON for the first time within one day.

Through the foregoing construction, unstable operation of the ultrasonic motor can be prevented without affecting the diagnostic operations by the user and life extension can be attempted.

Fourth Embodiment

Figure 6:
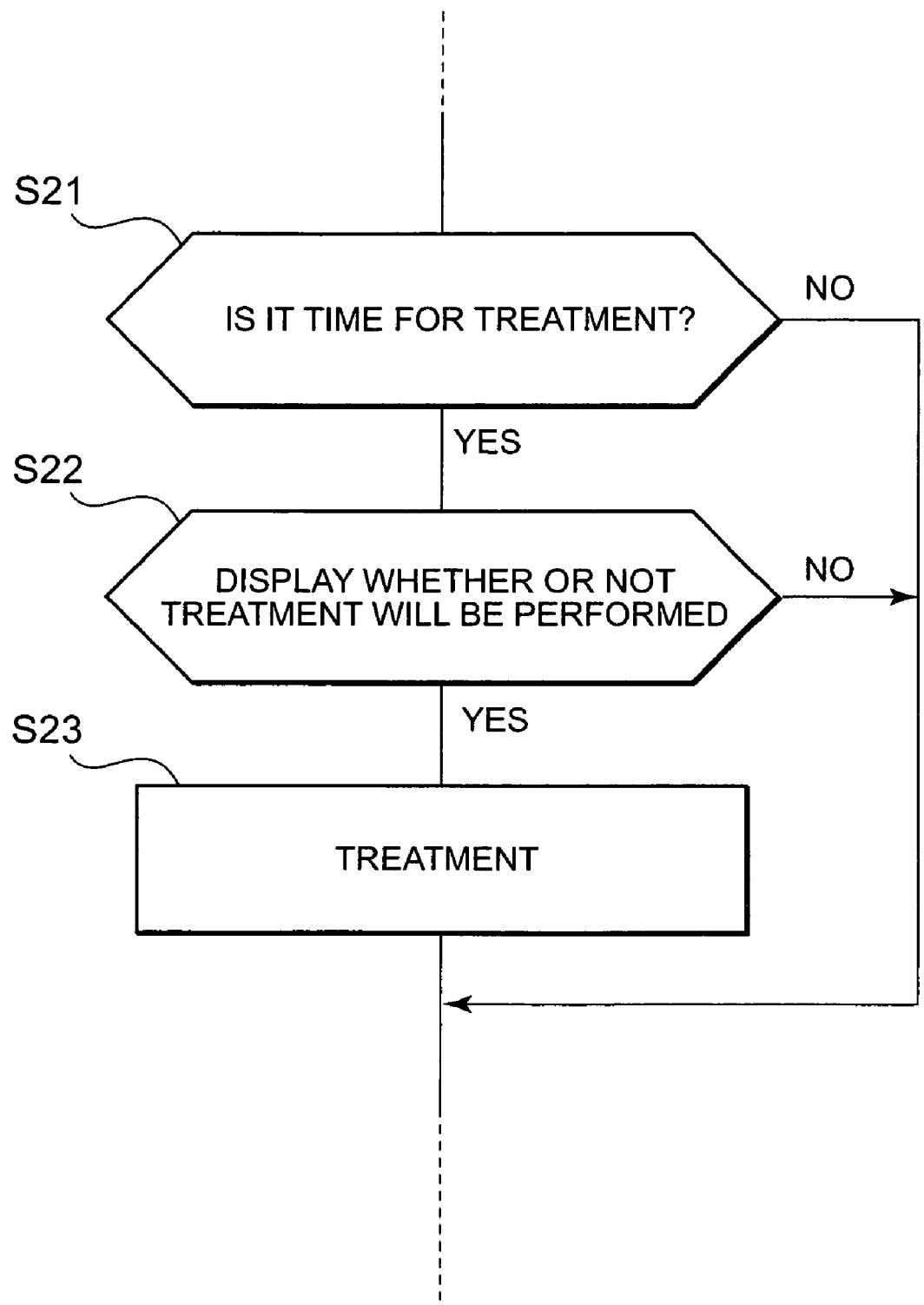
FIG. 6 is a flowchart explaining the processing of the ultrasonic diagnosis device according to a fourth embodiment of the present invention.

Next, a fourth embodiment is described with reference to FIG. 6. If the ultrasonic diagnostic device-side performs the treatment (high-speed rotation), diagnosis cannot be performed until the treatment is completed. Therefore, in the fourth embodiment, when it is time for treatment, the user is asked, beforehand, whether or not treatment should be performed, for example, by showing "perform"/"do not perform" treatment [a display part (lamp) can be provided in the probe main unit, or can be shown on the main unit display part] (step S21→S22), and treatment is performed (step S23) only when the user selects "perform".

Through the foregoing construction, unstable operation of the ultrasonic motor can be prevented without affecting the diagnostic operations by the user and life extension can be attempted.

Fifth Embodiment

Incidentally, in the ultrasonic diagnostic device, a plurality of ultrasonic probes 1 can be connected to the ultrasonic diagnostic device main unit 10, and the user generally selects and uses one out of these. Therefore, treatment can be preformed on ultrasonic probes 1 which are not in use.

Through the foregoing construction, unstable operation of the ultrasonic motor can be prevented without affecting the diagnostic operations by the user and life extension can be attempted.

INDUSTRIAL APPLICABILITY

According to the present invention, unstable operation of the ultrasonic motor can be prevented, when the ultrasonic motor is driven at the lower speed out of at least two types of speeds, and life extension can be attempted.

The invention claimed is:

1. An ultrasonic diagnostic device for obtaining three-dimensional images by scanning sonic elements by driving an ultrasonic motor, the device comprising:
    a speed control section that drives said ultrasonic motor at at least two different speeds;
    a timer for measuring an accumulated driving time at a lowest speed among said at least two different speeds;
    a determining section that determines whether or not said accumulated driving time exceeds a predetermined period of time, when a power switch of the ultrasonic diagnostic device has been turned OFF; and
    a high-speed rotation instructing section that applies to said speed control section an instruction for driving said ultrasonic motor at a highest speed among said at least two different speeds when it has been determined by said determining section that said accumulated driving time exceeds the predetermined period of time.

2. An ultrasonic diagnostic device for obtaining three-dimensional images by scanning sonic elements by driving an ultrasonic motor, the device comprising:
    a speed control section that drives said ultrasonic motor at at least two different speeds;
    a timer for measuring an accumulated driving time at a lowest speed among said at least two different speeds;
    a determining section that determines whether or not said accumulated driving time exceeds a predetermined period of time, when a screen saver of a monitor for displaying said three-dimensional images has been turned ON; and a high-speed rotation instructing section that applies to said speed control section an instruction for driving said ultrasonic motor at a highest speed among said at least two different speeds when it has been determined by said determining section that said accumulated driving time exceeds the predetermined period of time.

3. An ultrasonic diagnostic device for obtaining three-dimensional images by scanning sonic elements by driving an ultrasonic motor, the device comprising:

a speed control section that drives said ultrasonic motor at at least two different speeds;

a timer for measuring an accumulated driving time at a lowest speed among said at least two different speeds;

a determining section that determines whether or not said accumulated driving time exceeds a predetermined period of time, when a power switch of the ultrasonic diagnostic device has been turned ON for the first time within one day; and a high-speed rotation instructing section that applies to said speed control section an instruction for driving said ultrasonic motor at a highest speed among said at least two different speeds when it has been determined by said determining section that said accumulated driving time exceeds the predetermined period of time.

4. An ultrasonic diagnostic device for obtaining three-dimensional images by scanning sonic elements by driving an ultrasonic motor, the device comprising:

a speed control section that drives said ultrasonic motor at at least two different speeds;

a timer for measuring an accumulated driving time at a lowest speed among said at least two different speeds;

a determining section that determines whether or not said accumulated driving time exceeds a predetermined period of time;

a selecting section that makes it possible that one of turning on or not a drive instruction at a lowest speed among said at least two different speeds can be selected when it has been determined by said determining section that said accumulated driving time exceeds the predetermined period of time; and a high-speed rotation instructing section that applies to said speed control section an instruction for driving said ultrasonic motor at a highest speed among said at least two different speeds when turning on said drive instruction at said lowest speed has been selected using said selecting section.

* * * * *